United States Patent
Johnson et al.

(10) Patent No.: US 10,096,076 B2
(45) Date of Patent: Oct. 9, 2018

(54) ANIMATED TIMELINE

(75) Inventors: Soren S. Johnson, Wakefield, MA (US); Erik Johnson, Bedford, NH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 746 days.

(21) Appl. No.: 13/376,607

(22) PCT Filed: May 17, 2010

(86) PCT No.: PCT/IB2010/052175
§ 371 (c)(1),
(2), (4) Date: Dec. 7, 2011

(87) PCT Pub. No.: WO2010/146485
PCT Pub. Date: Dec. 23, 2010

(65) Prior Publication Data
US 2012/0078665 A1    Mar. 29, 2012

Related U.S. Application Data

(60) Provisional application No. 61/218,481, filed on Jun. 19, 2009.

(51) Int. Cl.
*G16H 10/60* (2018.01)
*G06Q 50/24* (2012.01)
*G16H 40/63* (2018.01)

(52) U.S. Cl.
CPC ............. *G06Q 50/24* (2013.01); *G16H 40/63* (2018.01)

(58) Field of Classification Search
CPC ................................................. G06F 17/30064
See application file for complete search history.

(56) References Cited

U.S. PATENT DOCUMENTS

| 5,361,202 | A | * | 11/1994 | Doue | G06Q 50/24 |
|---|---|---|---|---|---|
| | | | | | 705/3 |
| 6,034,683 | A | * | 3/2000 | Mansour | G06Q 10/06 |
| | | | | | 715/764 |
| 6,061,062 | A | * | 5/2000 | Venolia | G06F 3/0481 |
| | | | | | 715/856 |

(Continued)

FOREIGN PATENT DOCUMENTS

| EP | 2051201 A1 | 4/2009 | | |
|---|---|---|---|---|
| WO | PCT/JP2007/064559 | * | 7/2007 | G06Q 50/00 |

OTHER PUBLICATIONS

Animated Graphics Definition: What are Animated Graphics, about. com, Sep. 30, 2013.*

(Continued)

*Primary Examiner* — Jason S Tiedeman

(57) ABSTRACT

When presenting information to a user via a display, an animated timeline (18) is provided on which a user selects a tick mark (74, 92) representing a time on the timeline (18), to view data collected at that time. A time window (72) of a predetermined width (e.g., an hour) is centered on the selected tick mark (74, 92), and the timeline (18) is then animated as it shifts the selected tick mark (74, 92) to the center of the timeline (18). Data (e.g., images, measured parameters, etc.) corresponding to the time window is identified (e.g., via timestamp information) and presented to the user on a display along with the timeline (18).

12 Claims, 6 Drawing Sheets

(56) References Cited

U.S. PATENT DOCUMENTS

| | | | |
|---|---|---|---|
| 6,336,900 B1* | 1/2002 | Alleckson | G06F 19/3418 600/485 |
| 6,339,900 B1* | 1/2002 | Weder | 47/72 |
| 6,392,651 B1* | 5/2002 | Stradley | G06F 3/0481 345/473 |
| 6,876,972 B1* | 4/2005 | Kameda | G06Q 50/24 705/3 |
| 7,328,411 B2* | 2/2008 | Satanek | G06F 3/04855 715/786 |
| 2003/0016248 A1* | 1/2003 | Hayes Ubillos | G06F 3/04847 715/800 |
| 2003/0034990 A1* | 2/2003 | Roelofs | G06T 11/206 345/660 |
| 2003/0038831 A1* | 2/2003 | Engelfriet | G06F 15/0266 715/719 |
| 2003/0158477 A1* | 8/2003 | Panescu | 600/424 |
| 2004/0169681 A1* | 9/2004 | Van Kesteren | G06F 3/0481 715/764 |
| 2005/0105374 A1* | 5/2005 | Finke-Anlauff | G06F 17/30274 365/232 |
| 2005/0108233 A1* | 5/2005 | Metsatahti | G06F 17/30014 |
| 2005/0108234 A1* | 5/2005 | Oksanen | G06F 3/0485 |
| 2005/0108253 A1* | 5/2005 | Metsatahti et al. | 707/100 |
| 2005/0138066 A1* | 6/2005 | Finke-Anlauff | G06F 17/30044 |
| 2006/0101384 A1* | 5/2006 | Sim-Tang | G06F 11/1448 717/104 |
| 2006/0224993 A1* | 10/2006 | Wong | G06F 17/30274 715/800 |
| 2007/0299945 A1* | 12/2007 | Lunsford | 709/223 |
| 2008/0306766 A1 | 12/2008 | Ozeki et al. | |
| 2009/0112292 A1* | 4/2009 | Armstrong | A61N 1/3706 607/63 |
| 2009/0127339 A1* | 5/2009 | Needhan | G06F 19/3456 235/454 |
| 2009/0177998 A1* | 7/2009 | Barrios | G06F 3/04855 715/799 |
| 2009/0254370 A1* | 10/2009 | Kondo | G06Q 10/06 705/3 |

OTHER PUBLICATIONS

Medical Imaging Informatics, Alex A.T. Bui, Ricky K. Taira (eds.), Springer, 2009, pp. 158-160.*

Adobe Studio on Photoshop CS2, Demonstrate concepts through animation, 3 pages, 2005.*

Krishnan et al., TimeSpace: activity-based temporal visualisation of personal information spaces, Pers Ubiquit Comput (2005) 9: 46-65.*

Mazur, R; Tools and APIs for Visualisation of Timelines; 2008; 4 pages; URL:http://web.science.mq.edu.au/mpawel/publications/pdf/Mazur_timelines_2008.pdf.

Shahar, Y., et al.; Distributed, intelligent, interactive visualization and exploration of time-oriented clinical data and their abstractions; 2006; Artificial Intelligence in Medicine; 38:115-135.

Bui, et al., "TimeLine: Visualizing Integrated Patient Records", IEEE Transactions on Information Technology in Biomedicine, vol. 11, No. 4, Jul. 1, 2007.

* cited by examiner

ANIMATED TIMELINE

CROSS REFERENCE TO RELATED APPLICATIONS

This application claims the benefit of U.S. provisional application Ser. No. 61/218,481 filed Jun. 19, 2009, which is incorporated herein by reference.

The present application finds particular utility in medical data systems. However, it will be appreciated that the described technique(s) may also find application in other types of medical systems, other data recall systems, and/or other applications in which historical data is employed.

Classical computer displays that provide a timeline for user navigation have several drawbacks. For instance, in order to select a time window to be displayed, a user typically drags a window start time indicator and a window stop time indicator to the appropriate location along the timeline. The timeline stays stationary with the current time at the right end of the timeline. While functional, adjusting the time period for review involves several click and drag operations.

Many software applications require some variation of a timeline control to select a specific time or a span of time, usually to view data in the corresponding time period. Often such timelines are annotated with points of interest, a summarized view of the data or some demarcation that is helpful for navigation.

Classical navigable timelines are not touch-screen friendly. Many current applications require the user to drag icons across the timeline to set the selected time or time span. This action is difficult on most touch-screens. Annotated timelines additionally have the problem that the selected time or time span is usually not in the exact center of the timeline. This means that the user typically sees more annotations before the selection than after it, or vice versa.

There is an unmet need in the art for systems and methods that facilitate automated time window centering on a navigable timeline display, and the like, thereby overcoming the deficiencies noted above.

In accordance with one aspect, a system that facilitates automatically centering a selected tick mark on a timeline for visual presentation to a user includes a processor that executes computer-executable instructions stored in a memory. The instructions include receiving information regarding a user-selected tick mark representing a time on a timeline, and centering a predefined time window on the selected tick mark. The instructions further include animating movement of the timeline while shifting the selected tick mark to the center of the timeline during a predetermined time period. The system also includes a display that presents the timeline to the user.

In accordance with another aspect, a method of automatically centering a selected tick mark on a timeline for visual presentation to a user includes receiving information regarding a user-selected tick mark that represents a time on a timeline, and centering a predefined time window on the selected tick mark. The method further includes animating movement of the timeline while shifting the selected tick mark to the center of the timeline during a predetermined time period, and displaying the timeline to the user.

One advantage is that contextual patient data is presented on either side of a selected time.

Another advantage resides in animating a timeline shift to alert a user that the timeline is shifting.

Still further advantages of the subject innovation will be appreciated by those of ordinary skill in the art upon reading and understand the following detailed description.

The drawings are only for purposes of illustrating various aspects and are not to be construed as limiting.

Figure 1:
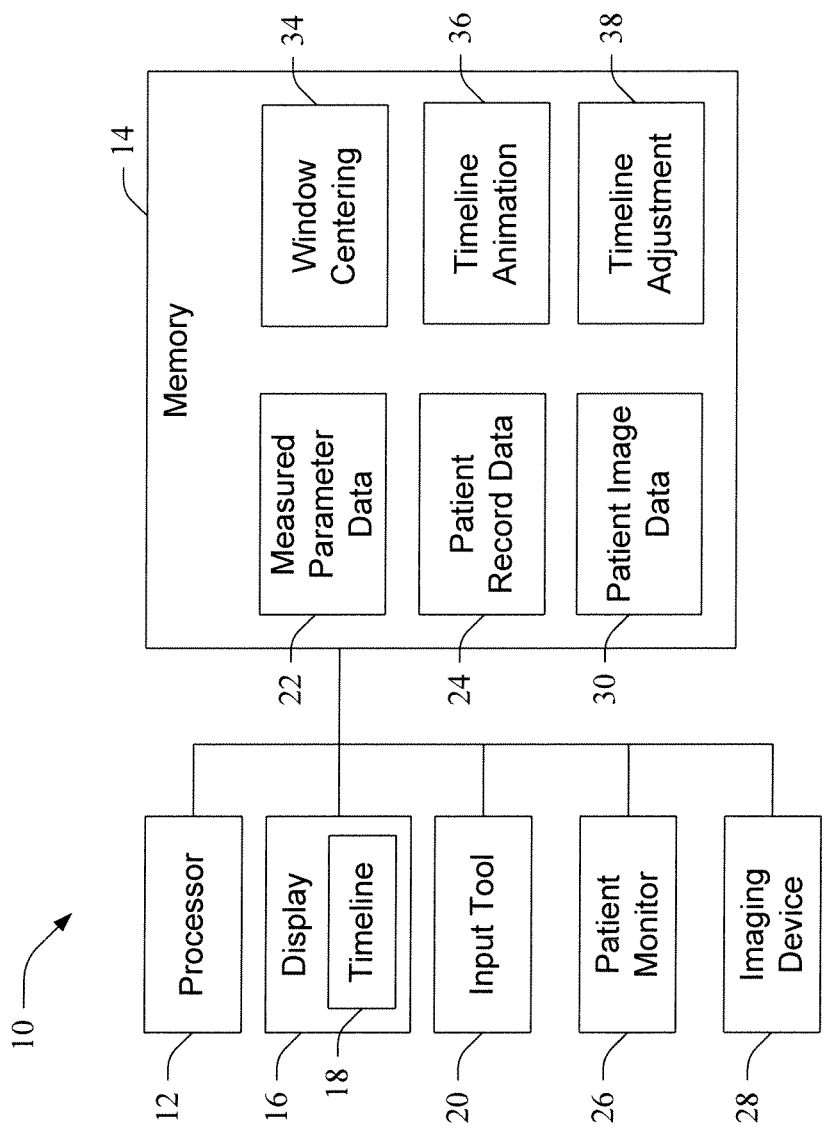
FIG. 1 illustrates a system for animating and automatically centering a timeline on a computer display by clicking on the time at the center of a desired window along the timeline.

FIG. 1 illustrates a system 10 for animating and automatically centering a timeline on a computer display by clicking on the time at the center of a desired window along the timeline. Data corresponding to a temporal window centered on the selected (e.g., clicked) time is immediately displayed on the screen. Animation is employed to smoothly shift the timeline indicator over a predetermined time period (e.g., about 1-3 seconds), such that the selected temporal window is transitioned into the center of the screen. The user can expand or contract the window by sliding window boundary tabs or by clicking on or entering a displayed window size (e.g., 1 hour, 2 hours, etc.). Since the window is positioned symmetrically about the center of the window, moving either of the boundary tabs can cause the other boundary tab to be moved symmetrically.

The system includes a processor 12 that executes, and a memory 14 that stores, computer executable instructions for carrying out the various functions and/or methods described herein. The memory 14 may be a computer-readable medium on which a control program is stored, such as a disk, hard drive, or the like. Common forms of computer-readable media include, for example, floppy disks, flexible disks, hard disks, magnetic tape, or any other magnetic storage medium, CD-ROM, DVD, or any other optical medium, RAM, ROM, PROM, EPROM, FLASH-EPROM, variants thereof, other memory chip or cartridge, or any other tangible medium from which the processor 12 can read and execute. In this context, the system 10 may be implemented on or as one or more general purpose computers, special purpose computer(s), a programmed microprocessor or microcontroller and peripheral integrated circuit elements, an ASIC or other integrated circuit, a digital signal processor, a hardwired electronic or logic circuit such as a discrete element circuit, a programmable logic device such as a PLD, PLA, FPGA, Graphical card CPU (GPU), or PAL, or the like.

A display 16 (e.g., a graphical user interface, a computer monitor, etc.) is coupled to the processor 12 and memory 14, and a timeline 18 is presented thereon to a user. The user manipulates an input tool 20 (e.g., a keyboard, mouse, stylus, directional pad, or the like) to select a time on the timeline 18 to view patient record data 22 and/or measured parameter data 24 for a predefined time window about the selected time. For example, if the user selects 4 pm and the predefined time window is one hour, then the time window will be centered on 4 pm and the display will show patient data and/or measured parameter data for the time window from 3:30 pm to 4:30 pm. Patient record data may include, without being limited to, patient identification information, patient medication(s), doses (e.g., sizes and/or times), and any other relevant patient information. Measured parameter data may include, without being limited to, heart rate, respiratory rate, electrocardiogram (ECG) data, blood-oxygen level (SpO2), blood glucose level, temperature, blood pressure, or any other patient parameter than can be measured by a patient monitor 26.

Additionally, the system 10 includes an imaging device 28 (e.g., a digital camera, an ultrasound device, a magnetic resonance imager, nuclear imager, an X-ray device, a computed tomography device, or other imaging device) that generates images of a patient. Patient image data 30 is stored in the memory 14 for access by a user. It will be appreciated that measured parameter data 22, relevant patient record data 24, and patient image data 30 is time-stamped upon obtaining such data, and the timestamp information is stored to the memory 16 and employed by the processor to correlate patient data to a selected time window location.

According to an example, when a user opens the timeline application on a computer, the timeline is presented to the user with the time window at the far right of the timeline, such that a most recent predefined time period or window is presented. Additionally, measured parameter data 22, patient image data 30, and/or patient record data 24 obtained during the time window are presented to the user on the display. For instance, if the current time is 11 am, and the predefined time period is two hours, then the time window will span from 9 am to 11 am on the timeline, and patient parameter data such as heart rate, blood pressure, SpO2, and any other desired parameter measurements will be shown for the period beginning at 9 am and ending at 11 am. Additionally, the patient parameter date and timeline can be updated periodically or continuously while the user views the display. For instance, the timeline and parameter data can be updated every minute (or every N minutes where N is an integer), so that the user always has a current two-hour window of data on the display.

To further this example, if the user desires to see patient data for approximately 8 am, then the user clicks on, or otherwise selects, a point on the timeline corresponding to 8 am. The processor 12 accesses and/or executes a window centering algorithm 34 (e.g., a set of computer-executable instructions stored in the memory) that centers the time window on 8 am. The processor concurrently accesses and/or executes a timeline animation algorithm 36 that controls a speed at which the window is centered on the newly selected time (e.g., 8 am). In one embodiment, the timeline is animated to shift the window from the previously selected time (or default time upon timeline initiation) to the newly selected time over a predefined time period (e.g., 1 second, 2 seconds, etc.). In another embodiment, the window is shifted at a predefined rate (e.g., 4 hours per second, 2 hours per second, etc.). For instance, the if the predefined rate is 2 hours per second, then a shift from 10 am to 9 am will take approximately 0.5 seconds.

Once the time window is centered on the newly selected time, patient data (e.g., measured parameter data, patient image data, patient record data, etc.) having timestamps correlating to the time window is presented on the display for user review. In one embodiment, the patient data scrolls across the screen in time with the timeline animation of the time window shift. In another embodiment, the user can select a slow predefined window shifting rate, such as one hour per minute, which causes the patient data to be scrolled more slowly so that the user can view patient data trends between the original time and the newly selected time.

According to another embodiment, a "current time" icon or button is provided that, when selected by the user, causes the time window to shift as far to the right as possible. For instance, if the current time is 8 pm, and the time window is set at 30 minutes wide, then the time window will center on 7:45 pm so that incoming or current patient data is presented at the leading edge of the time window. The system updates the stored patient data periodically (e.g., every minute, 30 seconds, etc.) or continuously stores patient data to a real-time buffer.

In this manner, the system 10 facilitates streamlining the number of clicks or other actions required to navigate through time, which improves workflow and efficiency. Additionally, by keeping the time window centered on a selected time mark, a maximum of amount of context is presented on either side of the selected time mark. Moreover, the animated fashion in which a selected time mark with a time window centered thereon is shifted to the center of the timeline ensures that the user is not confused by the change. Clicking (or gesturing on a time mark on a touch screen) anywhere on the timeline causes the time window to be centered on the selected time, and begins animation of the timeline towards the center.

It will be appreciated that the described systems and methods can be applied to any application where time navigation is desired, and is particularly useful for touch-screen applications or applications where the timeline is annotated.

Figure 2:
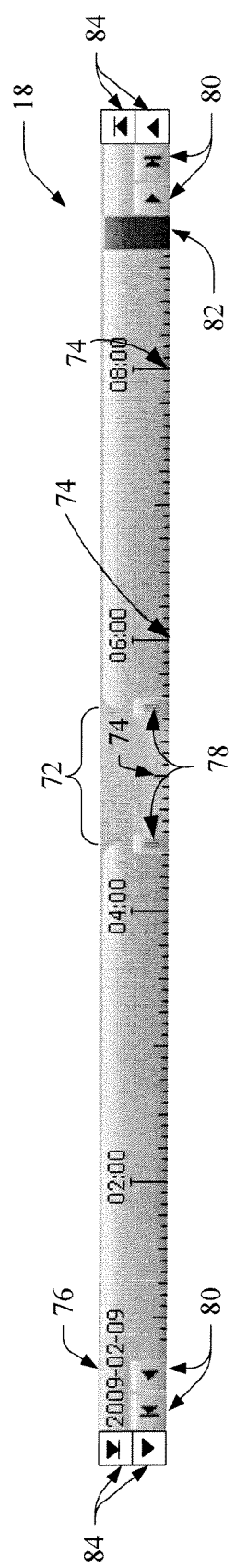
FIG. 2 illustrates an example of a timeline with a time window centered on approximately 5:00.

FIG. 2 illustrates an example of a timeline 18, with a time window 72 centered on approximately 5:00. The time window, in the illustrated example, is set to one hour. The timeline further includes a plurality of tick marks 74 that demarcate points in time. A date indicator 76 is also displayed on the timeline. Movable window boundary tabs 78 can be dragged to increase or decrease the duration (e.g., width) of the time window 72. Alternatively, the user can be presented with a time window duration selection or drop-down menu from which the user selects a window width or duration from a list of predetermined window durations.

The timeline optionally includes timeline shift buttons 80 that the user can click or select to move the timeline left, right, or to the beginning or end of the timeline. It will be noted that the user can also simply click on a tick mark 84 to shift the timeline to the desired time, and the time window is automatically centered on the selected tick mark.

One or more colored demarcations 82 are presented on the timeline and can be clicked to retrieve a data summary or other useful information for the user. Additionally, selectable or clickable zoom buttons 84 are presented to the user to permit graduated zooming in or out on the timeline, as well as complete zooming in or out. For instance, the zoom feature permits the user to widen or narrow the time window without having to move one or both of the boundary tabs 78. According to an example, if the time window is preset to one hour, and the user is viewing ECG data collected during a selected hour, a heart rate of 60 beats per minute will yield 3600 beats on the display. The user employs the zoom buttons to zoom in by a desired amount to view individual heartbeats in the ECG data. In another example, if the user is viewing blood pressure data corresponding to an hour-long time window, and blood pressure measurements are taken every 15 minutes, the user will only be presented with four blood pressure measurements for the selected hour. In this case the user employs the zoom buttons to zoom out (e.g., increase the width of the time window) to view as many blood pressure readings as the user desires in order to view a trend in blood pressure.

According to one embodiment, zoom control is provided by a scroll wheel on a mouse or the like. For instance, using a mouse, the user can position a cursor over a tick mark 74 in the time window 72, and can then scroll upward (e.g., away from the user) to zoom in or downward to zoom out, or vice versa.

Figure 3:
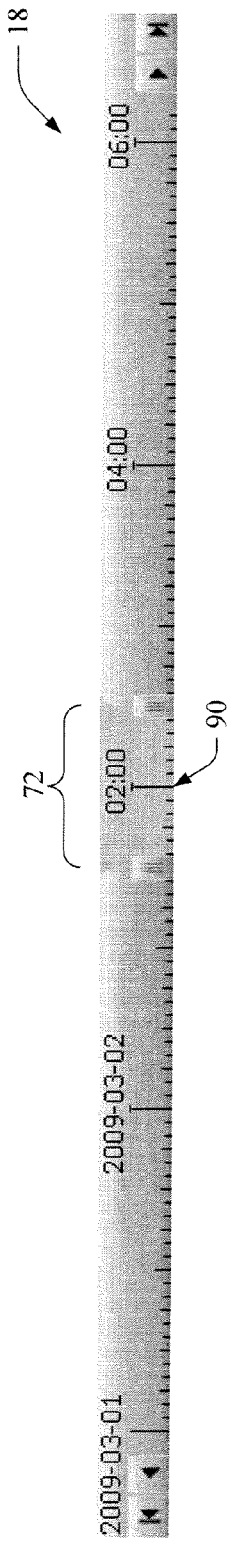
FIG. 3 illustrates the time window centered on the 2:00 tick mark.
Figure 4:
FIG. 4 illustrates a timeline in which a user has selected the 4:00 tick mark, and the time window has shifted so that it is centered thereon.
Figure 5:
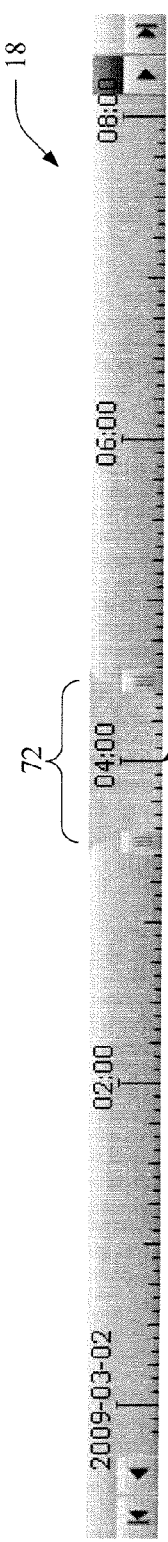
FIG. 5 illustrates the timeline shifted so that the 4:00 tick mark is centered on the timeline, with the time window still centered around the 4:00 tick mark.

FIGS. 3-5 illustrate the timeline 18 in various stages of animation, in accordance with various aspects described herein. In FIG. 3, the time window 72 is centered on the 2:00 tick mark 90. In FIG. 4, a user has selected the 4:00 tick mark 92, and the time window 72 starts shifting left. In FIG. 5, the timeline 18 has shifted so that the 4:00 tick mark 92 is centered on the timeline, with the time window 72 still centered on the 4:00 tick mark. One or both of the time window shift and the timeline shift is animated such that the shift occurs over a predefined time period (e.g., on the order of one or a few seconds, etc.).

Figure 6:
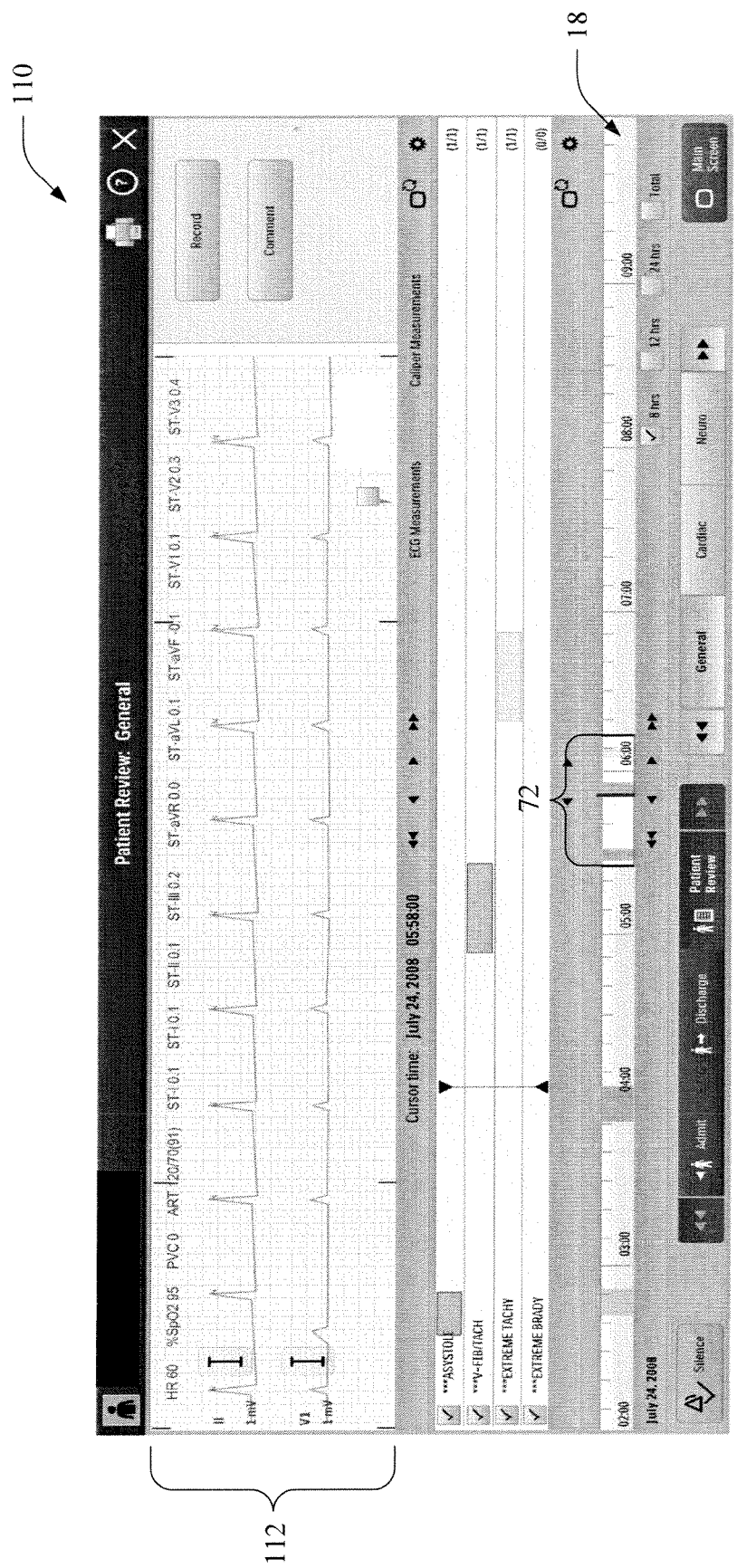
FIG. 6 is a screenshot showing patient information that may be displayed to a user with the timeline, according to various aspects described herein.

FIG. 6 is a screenshot 110 showing patient information that may be displayed to a user with the timeline 18, according to various aspects described herein. The time window 72 is centered on the timeline at approximately the 5:50 mark, and has a span of approximately 50 minutes. Patient data 112 (e.g., heart rate, blood pressure, SpO2, respiratory rate, temperature, or any other measurable patient data) is displayed for the 50 minute span of the time window.

Figure 7:
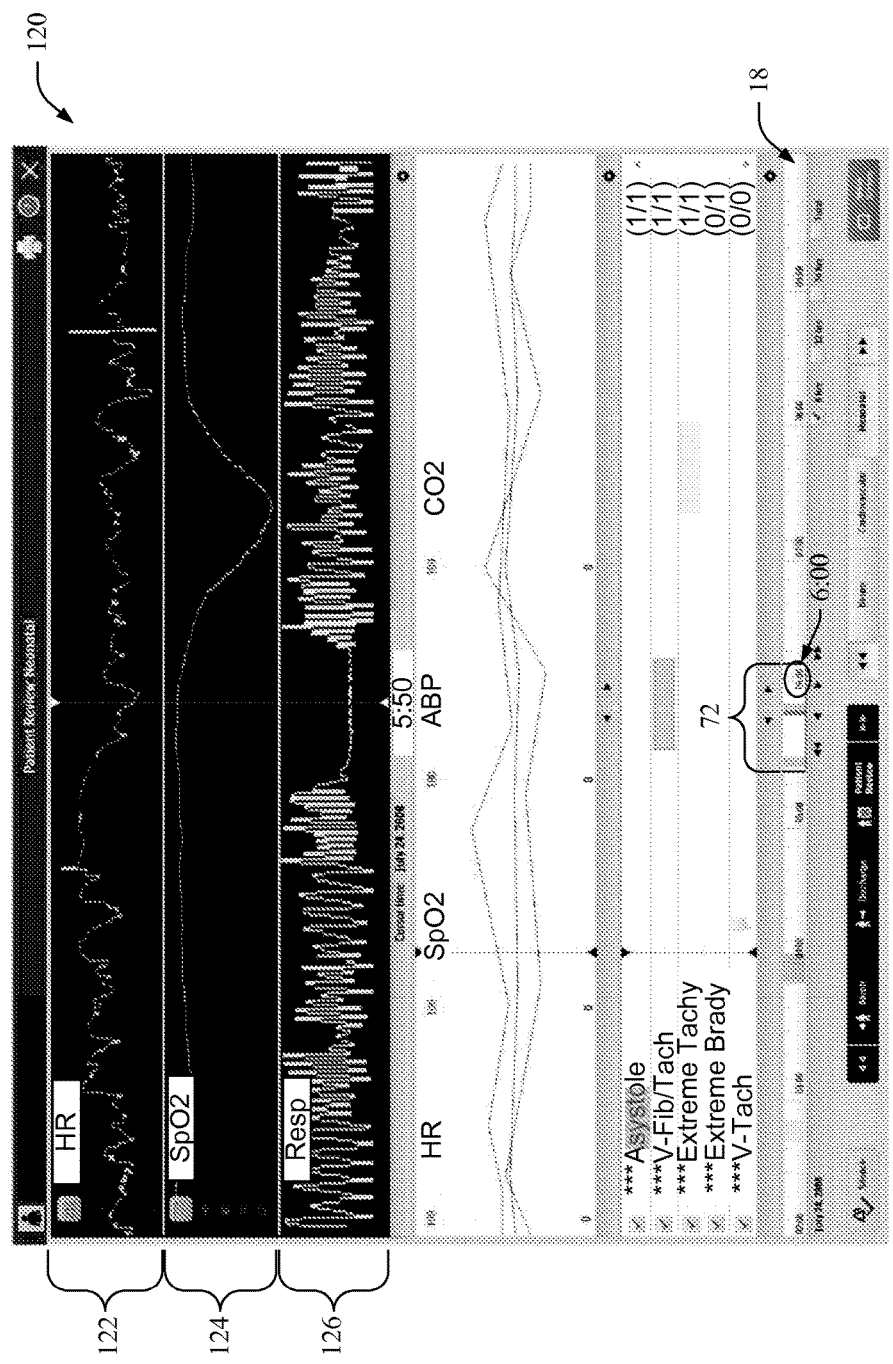
FIG. 7 is a screenshot showing measured patient parameter data that is displayed to a user reviewing a segment of the timeline, in accordance with various aspects described herein.

FIG. 7 is a screenshot 120 showing measured patient parameter data that is displayed to a user reviewing a segment of the timeline 18, in accordance with various aspects described herein. The time window 72 is approximately 50 minutes in duration, and is centered at approximately the 5:50 mark. The patient data displayed for the selected time window includes hear rate data 122, SpO2 data 124, and respiration rate data 126.

Figure 8:
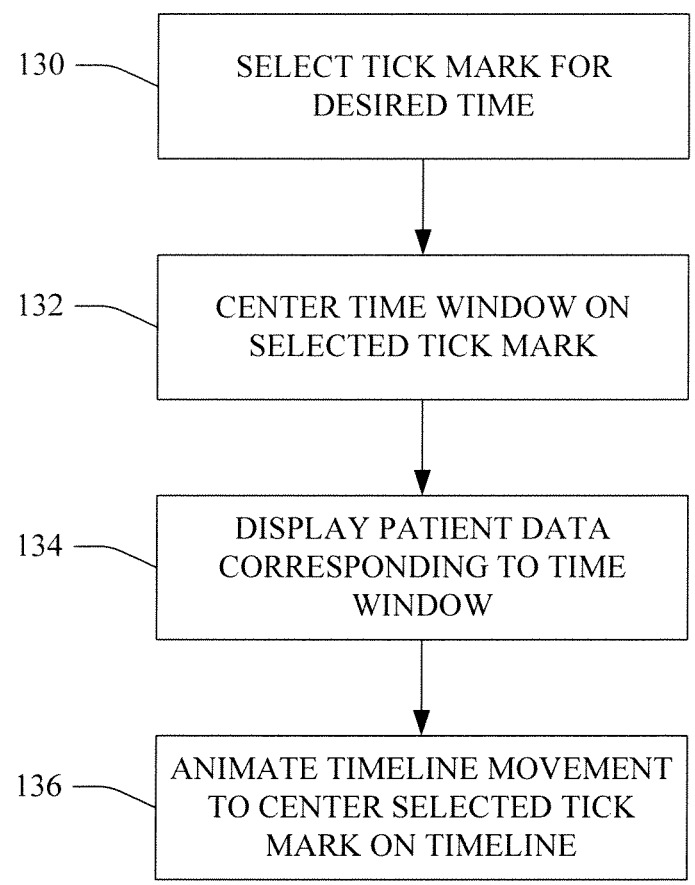
FIG. 8 illustrates a method of animating a timeline shift to ensure that a user is aware of the shift.

FIG. 8 illustrates a method of animating a timeline shift to ensure that a user is aware of the shift. At 130, a user selects a time (e.g., a tick mark or the like) on a timeline display (e.g., on a computer screen or other interface). Selection of the tick mark can be performed using a mouse, a stylus, directional arrow keys, touch screen, a touch pad, a joy stick, or in some other suitable manner. At 132, a time window having a predefined duration (e.g., 30 minutes, one hour, four hours, etc.) is centered on the selected tick mark. The time window is user-adjustable. At 134, patient data (e.g., measured patient parameters, patient record information, patient image data, etc.) corresponding to the time window is displayed to the user, along with the timeline. At 136, the timeline is shifted so that the selected tick mark is centered on the timeline. Shifting of the timeline occurs in an animated fashion over a predetermined time period or at a predetermined rate, so that the user sees the timeline moving until the selected tick mark is centered.

According to an example, a user selects a tick mark representing 4 am on the timeline. In this example, the timeline is centered at 12 pm, on the same day, prior to user selection of the 4 am tick mark. Upon selection of the tick mark, the time window is centered on the 4 am tick mark. This action may or may not be animated, as a matter of designer preference. The timeline then shifts (to the right, in this example) until the 4 am tick mark is centered on the timeline. Shifting of the timeline is animated so that the user sees the timeline moving to the right until the 4 am tick mark is centered on the timeline. Concurrently or subsequently, patient data corresponding to the time window is displayed to the user. For instance, if the time window is 30 minutes wide, then patient data measurements and/or images collected between 3:45 am and 4:15 am are presented to the user.

The innovation has been described with reference to several embodiments. Modifications and alterations may occur to others upon reading and understanding the preceding detailed description. It is intended that the innovation be construed as including all such modifications and alterations insofar as they come within the scope of the appended claims or the equivalents thereof.

Having thus described the preferred embodiments, the invention is now claimed to be:

1. A system that facilitates animating and automatically centering a selected tick mark on a timeline for visual presentation to a user, including:
   a processor that executes computer-executable instructions stored in a non-transitory memory, the instructions including:
      receiving, from an input tool with which the user selects a tick mark, information regarding a user-selected tick mark representing a time on the timeline, which is linear and comprises a plurality of tick marks representing discrete points in time;
      receiving information regarding a user-selected time window duration having a start time and end time, the time window duration including the user-selected tick mark;
      centering the user-selected time window duration on the user-selected tick mark on the timeline as it is displayed to the user; and
      animating movement of the timeline while centering the user-selected tick mark on the timeline during a user-selected predetermined time period, wherein the animation includes one or more intermediate states between an initial timeline position and a final timeline position, wherein the animation of the timeline is displayed to the user as the timeline appears to shift during the user-selected predetermined time period from the initial position to the final position in a manner that is perceptible to the user, and wherein the time window remains centered on the user-selected tick mark during the animation as the user-selected tick mark is shifted;
   an imaging device that generates images of a patient; and
   a display that presents the timeline and one or more generated images to the user;
   wherein the processor timestamps and stores the images to a memory and wherein the processor identifies patient image data corresponding to the user-selected time window duration, and outputs the identified patient image data to the display, where it is presented to the user; and further including
   a patient monitor that measures patient parameter data;
   wherein the processor timestamps and stores the measured patient parameter data to a memory; and
   wherein the processor identifies measured parameter data having timestamps corresponding to the predefined time window, and outputs the identified measured parameter data to the display, where it is presented to the user.

2. The system according to claim 1, wherein the predetermined time period is approximately 0.5-3 seconds in duration.

3. The system according to claim 1, wherein the measured parameter data includes at least one of:
blood pressure;
heart rate;
respiratory rate;
blood-oxygen level (SpO2);
temperature;
blood glucose level; and
electrocardiographic (ECG) data.

4. The system according to claim 1, wherein the predefined time window has a span in the range of 1 second to 24 hours.

5. The system according to claim 1, wherein the imaging device includes at least one of:
a digital camera;
an ultrasound device;
an X-ray device;
a computed tomography (CT) imaging device;
a magnetic resonance imaging (MRI) device; and
a nuclear imaging device.

6. The system according to claim 1, wherein the input tool is at least one of a mouse, a stylus, a touch screen, a touch pad, and a joy stick.

7. A method of animating and automatically centering a selected tick mark on a timeline for visual presentation to a user, including:
receiving information regarding a user-selected tick mark that represents a time on the timeline;
receiving, from an input tool with which the user selects a tick mark, information regarding a selected time window duration, the time window duration including the user-selected tick mark;
centering the user-selected the time window duration on the user-selected tick mark on the timeline as it is displayed to the user;
animating, via a processor, movement of the timeline while centering the user-selected tick mark on the timeline during a user-selected predetermined time period, wherein the animation includes one or more intermediate states between an initial timeline position and a final timeline position, wherein the animation of the timeline is displayed to the user as the timeline appears to shift during the user-selected predetermined time period from the initial position to the final position in a manner that is perceptible to the user, and wherein the time window remains centered on the user-selected tick mark during the animation as the user-selected tick mark is shifted;
displaying the timeline to the user on a display;
generating images of a patient;
timestamping the images;
storing the images to a memory;
identifying patient image data corresponding to the user-selected time window duration;
outputting the identified patient image data to the display;
displaying the identified patient image data to the user on the display;
measuring patient parameter data;
timestamping measured patient parameter data; and
storing the measured patient parameter data to a memory;
identifying measured parameter data having timestamps corresponding to the predefined time window;
outputting the identified measured parameter data to a display; and
displaying the measured parameter data to the user.

8. The method according to claim 7, wherein the predetermined time period is approximately 0.5-3 seconds in duration.

9. The method according to claim 7, wherein the measured parameter data includes at least one of:
blood pressure;
heart rate;
respiratory rate;
blood-oxygen level (SpO2);
temperature;
blood glucose level; and
electrocardiographic (ECG) data.

10. The method according to claim 7, wherein the predefined time window has a span in the range of 1 second to 24 hours.

11. The method according to claim 7, wherein the tick mark is selected using at least one of a mouse and a stylus.

12. A non-transitory computer-readable medium carrying software that controls a processor to:
receive information regarding a user-selected tick mark that represents a time on the timeline;
receive, from an input tool with which the user selects a tick mark, information regarding a selected time window duration, the time window duration including the user-selected tick mark;
center the user-selected time window duration on the user-selected tick mark on the timeline as it is displayed to the user;
animate, via a processor, movement of the timeline while centering the user-selected tick mark on the timeline during a user-selected predetermined time period, wherein the animation includes one or more intermediate states between an initial timeline position and a final timeline position, wherein the animation of the timeline is displayed to the user as the timeline appears to shift during the user-selected predetermined time period from the initial position to the final position in a manner that is perceptible to the user, and wherein the time window remains centered on the user-selected tick mark during the animation as the user-selected tick mark is shifted;
display the timeline to the user on a display;
generate images of a patient;
timestamp the images;
store the images to a memory;
identify patient image data corresponding to the user-selected time window duration;
output the identified patient image data to the display;
display the identified patient image data to the user on the display;
measure patient parameter data;
timestamp measured patient parameter data; and
store the measured patient parameter data to a memory;
identify measured parameter data having timestamps corresponding to the predefined time window;
output the identified measured parameter data to a display; and
display the measured parameter data to the user.

* * * * *